(12) United States Patent
Liu

(10) Patent No.: US 11,717,594 B2
(45) Date of Patent: Aug. 8, 2023

(54) ANTIMICROBIAL MEDICAL BIOMATERIAL AND A METHOD FOR PREPARING THE SAME

(71) Applicant: B. J. ZH. F. Panther Medical Equipment Co., Ltd., Beijing (CN)

(72) Inventor: Qing Liu, Beijing (CN)

(73) Assignee: B. J. ZH. F. PANTHER MEDICAL EQUIPMENT CO., LTD., Beijing (CN)

(*) Notice: Subject to any disclaimer, the term of this patent is extended or adjusted under 35 U.S.C. 154(b) by 109 days.

(21) Appl. No.: 17/170,013

(22) Filed: Feb. 8, 2021

(65) Prior Publication Data

US 2021/0322639 A1    Oct. 21, 2021

(30) Foreign Application Priority Data

Apr. 15, 2020    (CN) .......................... 202010292857.0

(51) Int. Cl.
| | |
|---|---|
| *A61L 27/36* | (2006.01) |
| *A61L 24/00* | (2006.01) |
| *A61L 15/44* | (2006.01) |
| *A61K 33/38* | (2006.01) |
| *A61L 15/20* | (2006.01) |
| *A61L 27/54* | (2006.01) |
| *A61L 15/40* | (2006.01) |
| *A61L 27/52* | (2006.01) |

(52) U.S. Cl.
CPC .......... *A61L 27/3629* (2013.01); *A61K 33/38* (2013.01); *A61L 15/20* (2013.01); *A61L 15/40* (2013.01); *A61L 15/44* (2013.01); *A61L 24/0005* (2013.01); *A61L 24/0015* (2013.01); *A61L 27/3687* (2013.01); *A61L 27/3691* (2013.01); *A61L 27/52* (2013.01); *A61L 27/54* (2013.01); *A61L 2300/104* (2013.01); *A61L 2300/216* (2013.01); *A61L 2300/404* (2013.01); *A61L 2430/34* (2013.01)

(58) Field of Classification Search
CPC ...... A61L 27/3629; A61L 27/52; A61K 33/38
See application file for complete search history.

(56) References Cited

U.S. PATENT DOCUMENTS

| | | | |
|---|---|---|---|
| 2010/0266654 A1 | 10/2010 | Hodde et al. | |
| 2014/0234388 A1* | 8/2014 | Christ ................... | A61K 33/26 264/41 |

FOREIGN PATENT DOCUMENTS

| | | | |
|---|---|---|---|
| CN | 109331228 A | * | 2/2019 |
| CN | 210114574 U | | 2/2020 |
| WO | 9836784 A1 | | 8/1998 |
| WO | 2007048099 A2 | | 4/2007 |
| WO | 2018013595 A1 | | 1/2018 |

OTHER PUBLICATIONS

Search Report for Chinese Application No. 202010292857.0; dated Nov. 6, 2020; 15 pgs.

* cited by examiner

*Primary Examiner* — Kyle A Purdy
(74) *Attorney, Agent, or Firm* — Hauptman Ham, LLP

(57) ABSTRACT

An antibacterial medical biomaterial includes an acellular small intestinal submucosal matrix material, an antibacterial gel layer located on a surface of the acellular small intestinal submucosal matrix material, and an absorbable fiber layer located on a surface of the antibacterial gel layer. Sulfadiazine silver is on the surface of the acellular small intestinal submucosal matrix material and/or within the acellular small intestinal submucosal matrix material. An absorbable fiber layer to which the sulfadiazine silver is attached, wherein the content of sulfadiazine silver in the absorbable fiber is 1 wt. %~2 wt. %. The medical biomaterial is usable as an external medicine for treating wound infections relayed by burns or wounds, and for reducing the incidence of infection by using a conventional central venous catheter with a sulfadiazine silver antibacterial coating, so that the medical biomaterial loaded with sulfadiazine silver also has antibacterial activity consistent with sulfadiazine silver.

7 Claims, 1 Drawing Sheet

ANTIMICROBIAL MEDICAL BIOMATERIAL AND A METHOD FOR PREPARING THE SAME

RELATED APPLICATIONS

The present application claims priority from Chinese Application Number 202010292857.0, filed Apr. 15, 2020, the disclosure of which is hereby incorporated by reference herein in its entirety.

TECHNICAL FIELD

The present invention relates to the technical field of medical biomaterials, and in particular to an antibacterial medical biomaterial and a method for preparing the same.

BACKGROUND

The defects of certain tissues or organs and partial or total loss of functions caused by various diseases and traumas are one of the main hazards to human health. Investigations and development of desirable materials for tissue repair is always an important problem in the fields of medical, bioscience, and material science. Currently, in a plurality of clinical medical biomaterials for tissue repair, an implantable medical biomaterial is a novel biomaterial leather capable of actively inducing tissue regeneration from a traditional non-absorbable material, and the extracellular matrix (ECM) material based on the principle of tissue engineering is a major development direction.

In the ECM material product entering the clinical application, the small intestinal submucosal (SIS) matrix material is the most ideal soft tissue repair material recognized by the academic demarcation, and the acellular SIS matrix material has a large sample amount of clinical application in the fields of abdominal wall repair, burn, anus, refractory wound, shaping procedure, pelvic floor repair, tendon repair, urogenital tract repair, neurorepair, etc. However, during the clinical application of the acellular SIS matrix material, the infections that may be generated are still problematic in the clinical problem, and therefore, the acellular SIS matrix material itself does not have antimicrobial and bacteriostatic capability, and it is easy to cause bacteria to adhere to the surface thereof, thereby causing relevant infections and linkage complications. Postoperative infections often occur even under conditions such as full sterilization of the operating room and strictly aseptic surgery.

Thus, it is necessary to develop an acellular SIS matrix material with antibacterial properties.

SUMMARY

The present invention provides an antibacterial medical biomaterial and a method for preparing the same.

In one aspect, the present invention provides an antibacterial medical biomaterial comprising an acellular small intestinal submucosal matrix material, an antibacterial gel layer located on a surface of the acellular small intestinal submucosal matrix material, and an absorbable fiber layer located on a surface of the antibacterial gel layer, sulfadiazine silver is dispersed on the surface of the acellular small intestinal submucosal matrix material and/or within the acellular small intestinal submucosal matrix material; the absorbable fiber layer comprises an absorbable fiber, to which the sulfadiazine silver is attached, wherein the content of sulfadiazine silver in the absorbable fiber is 1 wt. %~2 wt. %.

Further, the absorbable fiber layer has a thickness of 0.005 mm~0.05 mm;

Preferably, the absorbable fiber is one or more of hydroxyethyl cellulose, oxidized cellulose, and carboxymethyl fiber.

Further, the content of sulfadiazine silver in the acellular small intestinal submucosal matrix material is 2~5 wt. %.

Further, the acellular small intestinal submucosal matrix material is further loaded with one or more of chitosan, phenolsulfoethylamine, hemostatic polymer/compound, bioactive molecule, biomimetic active polypeptide molecule, polyamino acid, polydopamine, polyglycolide-trimethylene carbonate, polyglycolide and copolymers thereof, polycarbopron, poly L-lactide-caprolactone, polyglycolic acid, PPDO and polydioxanone (PDO).

Further, both sides of the antibacterial gel layer are combined with the acellular small intestinal submucosal matrix material and the absorbable fiber layer by hydrogen bonding;

the antibacterial gel layer comprises one or more of gelatin, polypeptide, protein, polyhistidine, fibrin and sodium hyaluronate, the thickness of the antibacterial gel layer is 0.001 mm~0.01 mm, and sulfadiazine silver is dispersed in the antibacterial gel layer, the content of sulfadiazine silver in the antibacterial gel layer is 2~5 wt. %, and the content of water in the antibacterial gel layer is 1~5%.

Another aspect of the present invention provides a method for preparing an antibacterial medical biomaterial, comprising:

a) placing the acellular small intestinal submucosal matrix material in a sodium hydroxide solution containing sulfadiazine, and controlling the pH of the solution between 7.1 and 13.0, so as to obtain an intermediate material covered with sodium sulfadiazine on the surface and/or inside thereof;

b) after removing the intermediate material obtained in step a from the solution, washing the same with a sodium chloride solution, and then performing a drying treatment, soaking the intermediate material in a silver nitrate solution, and substituting the sodium ions on the sulfadiazine sodium pyrimidine with the silver ions in the silver nitrate to obtain an acellular small intestinal submucosal matrix material loaded with sulfadiazine silver;

c) performing a surface plasma treatment on the acellular small intestinal submucosal matrix material loaded with sulfadiazine silver obtained in step b to hydroxylate the surface of the acellular small intestinal submucosal matrix material;

d) coating a layer of antibacterial gel layer on the surface of the acellular small intestinal submucosal matrix material in step c, wherein the antibacterial gel layer and the acellular small intestinal submucosal matrix material are combined by hydrogen bonding;

e) after the absorbable fibers are subjected to plasma treatment, preparing the absorbable fiber solution or gel liquid, and then stirring the sulfadiazine silver and the absorbable fiber solution or gel liquid uniformly to obtain a mixed solution or a mixed gel liquid;

f) coating the mixed solution or mixed gel liquid in step e on the surface of the acellular small intestinal submucosal matrix material with the antibacterial gel layer prepared in step d, and placing the acellular small intestinal submucosal matrix material in an oven or freeze-drying to obtain an antibacterial medical biomaterial.

Further, the step b further comprises: soaking the acellular small intestinal submucosal matrix material loaded with sulfadiazine silver in a compound buffer solution of PH 7.5~11.0. After the reaction is performed under the conditions of microwave irradiation, the surface of the acellular small intestinal submucosal matrix material loaded with sulfadiazine silver is formed with a compound film, washing and drying the submucosal matrix material of the small intestine mucosa loaded with sulfadiazine silver;

the compound buffer solution includes a buffer solution of one or more of chitosan, phenol sulfoethylamine, hemostatic polymer/compound, bioactive molecule, biomimetic active polypeptide molecule, polyamino acid, polydopamine, polyglycolide-trimethylene carbonate, polyglycolide and copolymers thereof, polycarbamone, poly L-lactide-caprolactone, polyglycolic acid, PPDO and polydioxanone (PDO).

Further, the reaction in steps a and b is performed in a thermostatic ultrasonic washer oscillating in a washing tank, and the ultrasonic shaking condition is that: 25~35° C. thermostatic reaction for 10~60 minutes, the oscillation frequency is 150~230 rpm, and the ultrasonic frequency is 40~50 kHz.

Further, the molar ratio of sulfadiazine to sodium hydroxide is 1:2~5, and the molar ratio of sulfadiazine to silver nitrate is 1:2~5.

Further, the method for preparing the acellular small intestinal submucosal matrix material comprises:

a1) immersing a small intestinal submucosal tissue material on an animal body into physiological saline for washing, placing a clean small intestinal submucosal tissue material into a closed container, and performing lyophilization sealing and sterilization storing on the small intestinal submucosal tissue material in liquid nitrogen;

b1) immersing the defrosted small intestinal submucosal tissue material into the decellularization solution for decellularization;

c1) ultrasonically cleaning the small intestinal submucosal tissue material after decellularization treatment in a sodium chloride solution, and stopping cleaning the small intestinal submucosal tissue material when the conductivity of the small intestinal submucosal tissue material is 1.5 um/s or less to obtain the small intestinal submucosal matrix material.

Preferably, when decellularization is performed by immersing the defrosted small intestinal submucosal tissue material into the decellularization solution, the decellularization is performed by treating the small intestinal submucosal tissue material obtained in step a1 with the decellularization solution in an environment containing two ultrasonic frequency wherein the decellularization solution comprises trypsin and PBS solution.

Wherein the mass percentage concentration of trypsin in the decellularization solution is 0.05~0.3%, the concentration of PBS solution is 0.5~1.5 mmol/L, and the pH value of the decellularization solution is 7.0~8.0.

Further, the decellularization process is performed in a dual-frequency ultrasonic apparatus, in which the low frequency range is 30~50 KHz, and the low frequency treatment for 10~45 min. the high frequency is 70~100 KHz, the high frequency treatment for 15~45 min, and the temperature range of the decellularization solution is 20~35° C.; ultrasonic power is 5000 W or more.

Further, the concentration of the sodium chloride solution is 0.01~0.05 mol/L, when the decellularized small intestinal submucosal tissue material is ultrasonically cleaned with sodium chloride solution.

The present invention provides an antibacterial medical biomaterial and a method for preparing the same. By loading the sulfadiazine silver on the acellular small intestinal submucosal matrix material, the acellular small intestinal submucosal matrix material loaded with sulfadiazine silver also has antimicrobial activity consistent with sulfadiazine silver. The antibacterial gel layer and the absorbable fiber layer are coated on the outer surface of the acellular small intestinal submucosal matrix material, so that the moisture-retaining function, liquid-absorbing function, hemostatic function, tear resistance and flexibility of the biomedical material of the biomaterial are improved. Sulfadiazine silver is attached to the absorbable fiber layer, so that the medical biomaterial provided by the present invention can be used as an external medicine for treating wound infections relayed by burns or wounds, and can also be used for reducing the incidence of infection by using a conventional central venous catheter with a sulfadiazine silver antibacterial coating. Therefore, the acellular small intestinal submucosal matrix material loaded with sulfadiazine silver also has antimicrobial activity consistent with sulfadiazine silver, thereby, the medical biomaterial provided by the present invention has antimicrobial and bacteriostatic capability.

Other features and advantages of the invention will be set forth in the description which follows and, in part, will be apparent from the description, or will be appreciated by practice of the invention. Objects and other advantages of the present invention may be achieved and obtained by structures particularly pointed out in the written description, claims, and drawings.

The technical solutions of the present invention will be further described in detail below with reference to the accompanying drawings and embodiments.

The figures are merely illustrative of the invention to facilitate understanding of the invention and are not intended to be limiting of the invention.

DETAILED DESCRIPTION

Hereinafter, specific embodiments of the present invention will be described in detail with reference to the accompanying drawings, but it should be understood that the scope of protection of the present invention is not limited by the specific embodiments.

Unless otherwise expressly indicated otherwise, throughout the description and claims, the term "comprise" or variations thereof such as "comprising" or "including" and the like will be understood to include the stated elements or components, but other elements or other components are not excluded.

Figure 1:
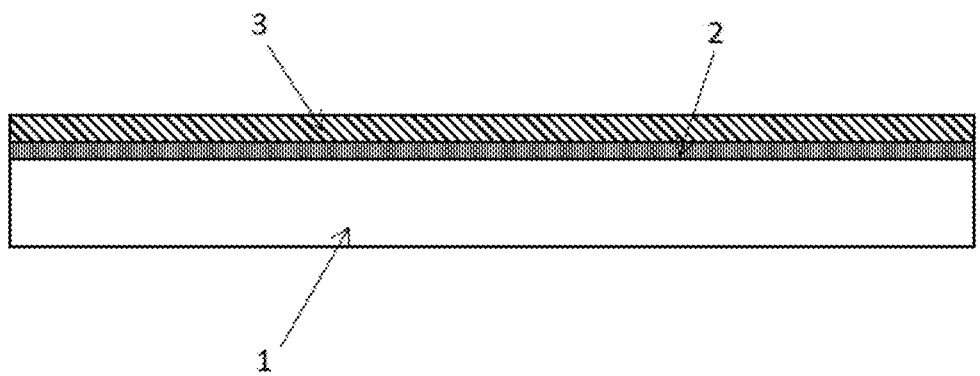
FIG. 1 is a schematic cross-sectional view of an antibacterial medical biomaterial according to an exemplary embodiment of the present invention.
Figure 2:
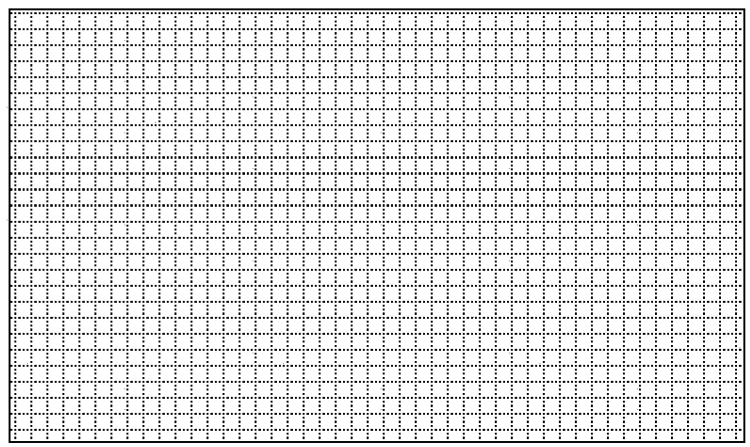
FIG. 2 is a schematic top view of an antibacterial medical biomaterial according to an exemplary embodiment of the present invention.

Referring to FIGS. 1 and 2, an aspect of the present invention provides an antibacterial medical biomaterial comprising an acellular small intestinal submucosal matrix material 1, an antibacterial gel layer 2 located on the surface of the acellular small intestinal submucosal matrix material 1, and an absorbable fiber layer 3 located on the surface of the antibacterial gel layer 2, sulfadiazine silver is dispersed on the surface of the acellular small intestinal submucosal matrix material 1 and/or within the acellular small intestinal submucosal matrix material 1; the absorbable fiber layer 3 comprises absorbable fibers to which sulfadiazine silver is attached, wherein the content of sulfadiazine silver in the absorbable fibers 3 is 1 wt. %~2 wt. %.

The absorbable fiber layer 3 has antibacterial properties by attaching sulfadiazine silver to the absorbable fiber, and the arrangement of the absorbable fiber layer 3 also improves the moisture-retaining function, liquid-absorbing function, hemostatic function, tear resistance and flexibility of the biomedical material. Since the sulfadiazine silver has good antimicrobial activity against most gram positive bacteria and negative bacteria, in addition to being widely used as an external medicine to treat wound infections secondary to burns or scalds, traditional central venous catheters can also be coated with sulfadiazine silver to reduce the incidence of infections, the acellular small intestinal submucosal matrix material loaded with sulfadiazine silver also has antimicrobial activity consistent with sulfadiazine silver, thereby, the medical biomaterial provided by the present invention has antimicrobial and bacteriostatic capability.

As a preferred embodiment, the absorbable fiber layer 3 has a thickness of 0.005 mm~0.05 mm;

Preferably, the absorbable fiber is one or more of hydroxyethyl cellulose, oxidized cellulose, and carboxymethyl fiber.

As a preferred embodiment, the content of sulfadiazine silver in the acellular small intestinal submucosal matrix material 1 is 2~5 wt. %.

In the present invention, the sulfadiazine silver is dispersed on the surface of the acellular small intestinal submucosal matrix material 1and/or within the acellular small intestinal submucosal matrix material 1, not only the capacity of loading of sulfadiazine silver is increased, but the durability of loading of sulfadiazine silver is also improved, so that the antibacterial medical biomaterial provided by the present invention maintains good antimicrobial performance for a long time.

As a preferred embodiment, the acellular small intestinal submucosal matrix material 1 is further loaded with one or more of chitosan, phenolsulfoethylamine, hemostatic polymer/compound, bioactive molecule, biomimetic active polypeptide molecule, polyamino acid, polydopamine, polyglycolide-trimethylene carbonate, polyglycolide and copolymers thereof, polycarbamone, poly L-lactide-caprolactone, polyglycolic acid, PPDO, and polydioxanone (PDO). In the present embodiment, the acellular small intestinal submucosal matrix material loaded with the above compound has various physiological functions such as antiinflammatory, bacteriostatic, hemostatic, anticancer, pro-growth, and enhanced immunity in addition to antibacterial properties.

As a preferred embodiment, both sides of the antibacterial gel layer 2 are combined with the acellular small intestinal submucosal matrix material 1 and the absorbable fiber layer 3 through hydrogen bonding.

The antibacterial gel layer 2 comprises one or more of gelatin, polypeptide, protein, polyhistidine, fibrin and sodium hyaluronate, the thickness of the antibacterial gel layer 2 is 0.001 mm~0.01 mm, and sulfadiazine silver is dispersed in the antibacterial gel layer 2, the content of sulfadiazine silver in the antibacterial gel layer 2 is 2~5 wt. %, and the content of water in the antibacterial gel layer is 1%~5%.

Another aspect of the present invention provides a method for preparing an antibacterial medical biomaterial, comprising:

a) placing the acellular small intestinal submucosal matrix material in a sodium hydroxide solution containing sulfadiazine, and controlling the pH of the solution between 7.1 and 13.0, so as to obtain an intermediate material loaded with sulfadiazine sodium on the surface and/or inside thereof;

b) after removing the intermediate material obtained in step a from the solution, washing the same with a sodium chloride solution, and then performing a drying treatment, soaking the intermediate material in a silver nitrate solution, and substituting the sodium ions on the sulfadiazine sodium with the silver ions in the silver nitrate to obtain an acellular small intestinal submucosal matrix material loaded with sulfadiazine silver;

c) performing a surface plasma treatment on the acellular small intestinal submucosal matrix material loaded with sulfadiazine silver obtained in step b to hydroxylate the surface of the acellular small intestinal submucosal matrix material;

d) coating a layer of antibacterial gel layer on the surface of the acellular small intestinal submucosal matrix material in step c, wherein the antibacterial gel layer and the acellular small intestinal submucosal matrix material are combined by hydrogen bonding;

e) after the absorbable fibers are subjected to plasma treatment, preparing the absorbable fiber solution or gel liquid, and then stirring the sulfadiazine silver and the absorbable fiber solution or gel liquid uniformly to obtain a mixed solution or a mixed gel liquid;

f) coating the mixed solution or mixed gel liquid in step e on the surface of the acellular small intestinal submucosal matrix material with the antibacterial gel layer prepared in step d, and placing the acellular small intestinal submucosal matrix material in an oven or freeze-drying to obtain an antibacterial medical biomaterial.

In the present invention, the acellular small intestinal mucosa is placed in a sodium hydroxide solution containing sulfadiazine, and the surface of the acellular small intestinal submucosal matrix material immersed in the solution is uniformly and firmly loaded with sulfadiazine sodium, so that the surface and/or the interior of the acellular small intestinal submucosal matrix material are coated with sulfadiazine sodium; then, the acellular small intestinal submucosal matrix material loaded with sulfadiazine sodium is placed in a silver nitrate solution, and the sodium ions on the sulfadiazine sodium are replaced by silver ions to generate sulfadiazine silver, the sodium ions and the nitrate form soluble sodium nitrate, the soluble sodium nitrate can be removed, and finally the sulfadiazine silver is synthesized in situ on the acellular small intestinal submucosal matrix material. In the method provided by the present invention, the sulfadiazine is not dissolved with the traditional aqueous ammonia, which has the following advantages: firstly, the corrosion effect of the aqueous ammonia on the acellular small intestinal submucosal matrix material can be avoided; second, stimulation and corrosion of ammonia water to mucous membranes such as eyes and nasal cavities of workers can be avoided; thirdly, an environmental problem caused by stimulating odor fumes evolving with high concentrations of ammonia can be avoided, and in this method, the loading capacity of sulfadiazine silver can be increased without using catalyst triflic acid or triflic acid salt, and the safety performance can be further improved.

As a preferred embodiment, the step b further comprises: soaking the acellular small intestinal submucosal matrix material loaded with sulfadiazine silver in a compound buffer solution of PH 7.5~11.0, after the reaction is performed under the conditions of microwave irradiation, the surface of the acellular small intestinal submucosal matrix material loaded with sulfadiazine silver is formed with a compound film, washing and drying the acellular small intestinal submucosal matrix material loaded with sulfadiazine silver;

wherein, the compound buffer solution includes a buffer solution of one or more of chitosan, phenolsulfoethylamine, hemostatic polymer/compound, bioactive molecule, biomimetic active polypeptide molecule, polyamino acid, polydopamine, polyglycolide-trimethylene carbonate, polyglycolide and copolymers thereof, polycarbamone, poly L-lactide-caprolactone, polyglycolic acid, PPDO and polydioxanone (PDO).

Upon microwave irradiation, the covalent bonding by the Michael addition reaction or the Schiff base reaction and the non-covalent bonding include a combination of van der Waals force and hydrogen bonding, so that the surface of the acellular small intestinal submucosal matrix material loaded with sulfadiazine silver soaked in the reaction liquid are uniformly and firmly loaded with compounds, thereby, the medical biomaterial prepared by the present invention also has various physiological functions such as anti-inflammatory, bacteriostatic, hemostatic, anticancer, pro-growth, bacteriostatic, and enhanced immunity in addition to antibacterial function.

As a preferred embodiment, the reactions in steps a and b are all performed in a thermostatic ultrasonic washer oscillating in a washing tank, and the ultrasonic shaking condition is that: 25~35° C. thermostatic reaction for 10~60 minutes, the oscillation frequency is 150~230 rpm, and the ultrasonic frequency is 40~50 kHz. In the present embodiment, the reaction in steps a and c is performed in a thermostatic ultrasonic washer capable of oscillating the cleaning tank. The effect of the synthesis reaction can be accelerated, especially when sulfadiazine silver is synthesized in situ, ultrasonic shaking can increase the probability of silver ions of silver nitrate to contact, react, and bond with sulfadiazine already firmly loaded on the acellular small intestinal submucosal matrix material by thousands. The synthesis of sulfadiazine silver is greatly promoted, and the time for synthesizing sulfadiazine silver in situ on the submucosa material of the acellular small intestine mucosa is shortened, and simplifying the step of synthesizing sulfadiazine silver in situ on the acellular small intestinal submucosal matrix material. Due to the use of ultrasonic shaking, no physical stirring and external warming are required in the reaction, thereby achieving molecular level stirring and high reaction yield.

As a preferred embodiment, the molar ratio of sulfadiazine to sodium hydroxide is 1:2~5, and the molar ratio of sulfadiazine to silver nitrate is 1:2~5.

As a preferred embodiment, the method for preparing the acellular small intestinal submucosal matrix material comprises:

a1) immersing a small intestinal submucosal tissue material on an animal body into physiological saline for washing, placing a clean small intestinal submucosal tissue material into a closed container, and performing lyophilization sealing and sterilization storing on the small intestinal submucosal tissue material in liquid nitrogen;

b1) immersing the defrosted small intestinal submucosal tissue material into the decellularization solution for decellularization;

c1) ultrasonically cleaning the small intestinal submucosal tissue material after decellularization treatment in a sodium chloride solution, and stopping cleaning the small intestinal submucosal tissue material when the conductivity of the small intestinal submucosal tissue material is 1.5 um/s or less to obtain the acellular small intestinal submucosal matrix material.

According to the present invention, the small intestine intercepted on the animal body is immersed in the 4° C. physiological saline for cleaning, preferably, the small intestine is removed and immediately after the small intestine is removed for cleaning, and the animal is not particularly limited, preferably pig, cattle, sheep, murine or horse.

As a preferable embodiment, when decellularization treatment is performed by immersing the defrosted small intestinal submucosal tissue material into the decellularization solution, the decellularization is performed by treating the small intestinal submucosal tissue material obtained in step a1 with the decellularization solution in an environment containing two ultrasonic frequency wherein the decellularization solution comprises trypsin and PBS solution.

As a preferred embodiment, the mass percentage concentration of trypsin in the decellularization solution is 0.05~0.3%, the concentration of PBS solution is 0.5~1.5 mmol/L, and the pH value of the decellularization solution is 7.0~8.0.

As a preferred embodiment, the decellularization process is performed in a dual-frequency ultrasonic apparatus, in which the low frequency range is 30~50 KHz, and the low frequency treatment for 10~45 min; the high frequency is 70~100 KHz, the high frequency treatment for 15~45 min, and the temperature range of the decellularization solution is 20~35° C.; ultrasonic power is 5000 W or more.

As a preferred embodiment, the concentration of the sodium chloride solution is 0.01~0.05 mol/L when the decellularized small intestinal submucosal tissue material is ultrasonically cleaned with sodium chloride solution.

As a preferred embodiment, the lyophilization temperature in step a1 is −75~−80° C., and the lyophilization time is 20~30 h.

As a preferred embodiment, the sterilization is to sterilize the sealed small intestinal submucosal tissue material through linear acceleration with a radiation dose of 8000 rads.

Hereinafter, an antibacterial medical biomaterial provided by the present invention will be described in detail by way of examples.

Example 1

A method for preparing an antibacterial medical biomaterial, comprising:

(1) immersing a small intestinal submucosal tissue material on a porcine body into physiological saline for washing, placing a clean small intestinal submucosal tissue material into a closed container, and performing lyophilization sealing and sterilization on the small intestinal submucosal tissue material in liquid nitrogen, wherein the lyophilization temperature is −75° C., the lyophilization time is 25 h, and the sterilization is to sterilize the sealed small intestinal submucosal tissue material through linear acceleration with a radiation dose of 8000 rads.

(2) treating the small intestinal submucosal tissue material obtained in step a1 with decellularization in an environment containing two ultrasonic frequencies with different frequencies for decellularization; wherein the decellularization solution comprises trypsin and PBS solution, the mass percentage concentration of trypsin in the decellularization solution is 0.05%, the concentration of PBS solution is 1 mmol/L, and the pH value of the decellularization solution is 7.0.

(3) ultrasonically cleaning the decellularized small intestinal submucosal tissue material in sodium chloride solution, the concentration of sodium chloride solution is 0.03 mol/L, and when the electrical conductivity of the small intestinal submucosal tissue material is 1.5 um/s or less, stopping cleaning the small intestinal submucosal tissue material to obtain the acellular small intestinal submucosal matrix material.

Wherein the decellularization process is performed in a dual-frequency ultrasonic apparatus, in which the low frequency range is 30 KHz and the low frequency treatment for 25 min, the high frequency is 90 KHz, the high frequency treatment for 15 min, and the temperature range of the decellularization solution is 30° C.; ultrasonic power is 5000 W or more.

(4) after placing the acellular small intestinal submucosal matrix material in a sodium hydroxide solution containing sulfadiazine, placing in a thermostatic ultrasonic washer capable of oscillating the cleaning tank, the pH of the solution was controlled to 7.1, and the temperature was controlled to 25° C. The reaction was performed for 10 minutes, the oscillation frequency was 150 rpm, and the ultrasonic frequency was 40 kHz. obtaining a surface and/or an intermediate material coated with sulfadiazine sodium, the molar ratio of sulfadiazine to sodium hydroxide is 1:2, the molar ratio of sulfadiazine to silver nitrate is 1:2.

(5) after the intermediate material is removed from the solution, the intermediate material is washed with a sodium chloride solution. After the drying treatment, the intermediate material is immersed in a silver nitrate solution, and placed in a thermostatic ultrasonic washer capable of oscillating the cleaning tank, the temperature was controlled to 25° C., the reaction was performed for 10 minutes, and the oscillation frequency was 150 rpm. The ultrasonic frequency is 40 KHz, and the sodium ions on the sulfadiazine sodium molecule are replaced by silver ions in silver nitrate. An acellular small intestinal submucosal matrix material loaded with sulfadiazine silver was obtained.

(6) performing a surface plasma treatment on the acellular small intestinal submucosal matrix material loaded with sulfadiazine silver, and so as to hydroxylate the surface of the acellular small intestinal submucosal matrix material.

(7) coating a layer of antibacterial gel layer on the surface of the acellular small intestinal submucosal matrix material, wherein the antibacterial gel layer and the acellular small intestinal submucosal matrix material are combined by hydrogen bonding.

(8) after the absorbable fibers are subjected to plasma treatment, preparing the absorbable fiber solution or gel liquid, and then stirring the sulfadiazine silver and the absorbable fiber solution or gel liquid uniformly to obtain a mixed solution or a mixed gel liquid.

(9) coating a mixed solution or a mixed gel liquid on the surface of the acellular small intestinal submucosal matrix material with the antibacterial gel layer, and placing the acellular small intestinal submucosal matrix material in an oven or freeze-drying to obtain an antibacterial medical biomaterial.

Wherein, the step 5 further comprises: soaking the acellular small intestinal submucosal matrix material loaded with sulfadiazine silver in a compound buffer solution of PH 7.5, performing a reaction under microwave irradiation conditions, and after the surface of the submucous matrix material of the acellular small intestine mucous membrane supported with sulfadiazine silver is formed with a compound film, the acellular small intestinal submucosal matrix material loaded with sulfadiazine silver is taken out, washed and dried;

The compound buffer solution includes a buffer solution of one or more of chitosan, phenol sulfoethylamine, hemostatic polymer/compound, bioactive molecule, biomimetic active polypeptide molecule, polyamino acid, polydopamine, polyglycolide-trimethylene carbonate, polyglycolide and copolymers thereof, polycarbamone, poly L-lactide-caprolactone, polyglycolic acid, PPDO and polydioxanone (PDO).

Example 2

A method for preparing an antibacterial medical biomaterial, comprising:

(1) immersing a small intestinal submucosal tissue material on a porcine body into physiological saline for washing, placing a clean small intestinal submucosal tissue material into a closed container, and performing lyophilization sealing and sterilization on the small intestinal submucosal tissue material in liquid nitrogen, wherein the lyophilization temperature is −78° C., the lyophilization time is 25 h, and the sterilization is to sterilize the sealed small intestinal submucosal tissue material through linear acceleration with a radiation dose of 8000 rads.

(2) treating the small intestinal submucosal tissue material obtained in step a1 with decellularization in an environment containing two ultrasonic frequencies with different frequencies for decellularization; wherein the decellularization solution comprises trypsin and PBS solution, the mass percentage concentration of trypsin in the decellularization solution is 0.2%, the concentration of PBS solution is 0.5 mmol/L, and the pH value of the decellularization solution is 7.0.

(3) ultrasonically cleaning the decellularized small intestinal submucosal tissue material in sodium chloride solution, the concentration of sodium chloride solution is 0.01 mol/L, and when the electrical conductivity of the small intestinal submucosal tissue material is 1.5 um/s or less, stopping cleaning the small intestinal submucosal tissue material to obtain the acellular small intestinal submucosal matrix material.

Wherein the decellularization process is performed in a dual-frequency ultrasonic apparatus, in which the low frequency range is 40 KHz and the low frequency treatment is 10 min. the high frequency is 70 KHz, the high frequency treatment is 35 min, and the temperature range of the decellularized liquid is 20° C. centigrade; Ultrasonic power is 5000 W or more.

(4) after placing the acellular small intestinal submucosal matrix material in a sodium hydroxide solution containing sulfadiazine, placing in a thermostatic ultrasonic washer capable of oscillating the cleaning tank, the pH of the solution was controlled to 11, the temperature was controlled to 30° C., and the reaction was performed for 30 minutes. The oscillation frequency is 200 rpm, and the ultrasonic frequency is 45 KHz, so as to obtain an intermediate material having a surface and/or an inner coated with sulfadiazine sodium. The molar ratio of sulfadiazine to sodium hydroxide is 1:3, the molar ratio of sulfadiazine to silver nitrate was 1:4.

(5) after the intermediate material is removed from the solution, the intermediate material is washed with a sodium chloride solution. After the drying treatment, the intermediate material is immersed in a silver nitrate solution, and placed in a thermostatic ultrasonic washer capable of oscillating the cleaning tank, the temperature was controlled to 30° C., the reaction was performed for 30 minutes, and the oscillation frequency was 200 rpm. The ultrasonic frequency is 45 KHZ, and the sodium ions on the sulfadiazine sodium molecule are replaced by silver ions in silver nitrate. An acellular small intestinal submucosal matrix material loaded with sulfadiazine silver was obtained.

(6) performing a surface plasma treatment on the acellular small intestinal submucosal matrix material loaded with sulfadiazine silver, and so as to hydroxylate the surface of the acellular small intestinal submucosal matrix material;

(7) coating a layer of antibacterial gel layer on the surface of the acellular small intestinal submucosal matrix material, wherein the antibacterial gel layer and the acellular small intestinal submucosal matrix material are combined by hydrogen bonding;

(8) after the absorbable fibers are subjected to plasma treatment, preparing the absorbable fiber solution or gel liquid, and then stirring the sulfadiazine silver and the absorbable fiber solution or gel liquid uniformly to obtain a mixed solution or a mixed gel liquid;

(9) coating a mixed solution or a mixed gel liquid on the surface of the acellular small intestinal submucosal matrix material with the antibacterial gel layer on the prepared surface, and placing the acellular small intestinal submucosal matrix material in an oven or freeze-drying to obtain an antibacterial medical biomaterial.

Wherein, the step 5 further comprises: soaking the acellular small intestinal submucosal matrix material loaded with sulfadiazine silver in a compound buffer solution having a pH of 9, performing a reaction under microwave irradiation conditions, and after the surface of the submucous matrix material of the acellular small intestine mucous membrane supported with sulfadiazine silver is formed with a compound film, the acellular small intestinal submucosal matrix material loaded with sulfadiazine silver is taken out, washed and dried;

The compound buffer solution includes a buffer solution of one or more of chitosan, phenol sulfoethylamine, hemostatic polymer/compound, bioactive molecule, biomimetic active polypeptide molecule, polyamino acid, polydopamine, polyglycolide-trimethylene carbonate, polyglycolide and copolymers thereof, polycarbamone, polyL-lactide-caprolactone, polyglycolic acid, PPDO and polydioxanone (PDO).

Example 3

A method for preparing an antibacterial medical biomaterial, comprising:

(1) immersing a small intestinal submucosal tissue material on a porcine body into physiological saline for washing, placing a clean small intestinal submucosal tissue material into a closed container, and performing lyophilization sealing and sterilization on the small intestinal submucosal tissue material in liquid nitrogen, wherein the lyophilization temperature is −80° C., the sterilization is to sterilize the sealed small intestinal submucosal tissue material through linear acceleration with a radiation dose of 8000 rads.

(2) treating the small intestinal submucosal tissue material obtained in step a1 with decellularization in an environment containing two ultrasonic frequencies with different frequencies for decellularization; wherein the decellularization solution comprises trypsin and PBS solution, the mass percentage concentration of trypsin in the decellularization solution is 0.3%, the concentration of PBS solution is 1.5 mmol/L, and the pH value of the decellularization solution is 8.0.

(3) ultrasonically cleaning the decellularized small intestinal submucosal tissue material in sodium chloride solution, the concentration of sodium chloride solution is 0.05 mol/L, and when the electrical conductivity of the small intestinal submucosal tissue material is 1.5 um/s or less, stopping cleaning the small intestinal submucosal tissue material to obtain the acellular small intestinal submucosal matrix material.

Wherein the decellularization process is performed in a dual-frequency ultrasonic apparatus, in which the low frequency range is 50 KHz and the low frequency treatment for 45 min; the high frequency is 100 KHz, the high frequency treatment for 45 min, and the temperature range of the decellularization solution is 35° C.; ultrasonic power is 5000 W or more.

(4) after placing the acellular small intestinal submucosal matrix material in a sodium hydroxide solution containing sulfadiazine, placing in a thermostatic ultrasonic washer capable of oscillating the cleaning tank, the pH of the solution was controlled to 13.0, the temperature was controlled to 35° C. centigrade, and the reaction was performed for 60 minutes, the oscillation frequency is 230 rpm, and the ultrasonic frequency is 50 KHz, so as to obtain an intermediate material having a surface and/or an inner coated with sulfadiazine sodium. The molar ratio of sulfadiazine to sodium hydroxide is 1:5. The molar ratio of sulfadiazine to silver nitrate was 1:5.

(5) after the intermediate material is removed from the solution, the intermediate material is washed with a sodium chloride solution. After the drying treatment, the intermediate material is immersed in a silver nitrate solution, and placed in a thermostatic ultrasonic washer capable of oscillating the cleaning tank, the temperature was controlled to 35° C. centigrade, the reaction was performed for 60 minutes, and the oscillation frequency was 230 rpm. The ultrasonic frequency is 50 KHZ, and the sodium ions on the sulfadiazine sodium molecule are replaced by silver ions in silver nitrate. An acellular small intestinal submucosal matrix material loaded with sulfadiazine silver was obtained.

(6) performing a surface plasma treatment on the acellular small intestinal submucosal matrix material loaded with sulfadiazine silver, and so as to hydroxylate the surface of the acellular small intestinal submucosal matrix material.

(7) coating a layer of antibacterial gel layer on the surface of the acellular small intestinal submucosal matrix material, wherein the antibacterial gel layer and the acellular small intestinal submucosal matrix material are combined by hydrogen bonding.

(8) after the absorbable fibers are subjected to plasma treatment, preparing the absorbable fiber solution or gel liquid, and then stirring the sulfadiazine silver and the absorbable fiber solution or gel liquid uniformly to obtain a mixed solution or a mixed gel liquid.

(9) coating a mixed solution or a mixed gel liquid on the surface of the acellular small intestinal submucosal matrix material with the antibacterial gel layer on the prepared surface, and placing the acellular small intestinal submucosal matrix material in an oven or freeze-drying to obtain an antibacterial medical biomaterial.

Wherein, the step 5 further comprises: soaking the acellular small intestinal submucosal matrix material loaded with sulfadiazine silver in a compound buffer solution having a pH of 11.0, performing a reaction under microwave irradiation conditions, and after the surface of the submucous matrix material of the acellular small intestine mucous membrane supported with sulfadiazine silver is formed with a compound film, the acellular small intestinal submucosal matrix material loaded with sulfadiazine silver is taken out, washed and dried;

The compound buffer solution includes a buffer solution of one or more of chitosan, phenol sulfoethylamine, hemostatic polymer/compound, bioactive molecule, biomimetic active polypeptide molecule, polyamino acid, polydopamine, polyglycolide-trimethylene carbonate, polyglycolide and copolymers thereof, polycarbamone, poly L-lactide-caprolactone, polyglycolic acid, PPDO and polydioxanone (PDO).

Product Antimicrobial Testing

The antibacterial activity of the antibacterial medical biomaterial prepared in the examples 1~3 is tested, and the test results are shown in table 1:

TABLE 1 results of antibacterial tests on the products of the examples

|  | Example 1 | Example 2 | Example 3 |
| --- | --- | --- | --- |
| Gram-positive bacteria | 96.9 | 96.3 | 97.1 |
| Negative bacteria | 97.8 | 98.1 | 97.9 |

The antibacterial property of the antibacterial medical biomaterial to gram-positive bacteria and gram-negative bacteria can still reach more than 95 percent, which shows that the medical biomaterial provided by the invention has good antibacterial effect.

Finally, it should be noted that the above embodiments are only for illustrating the technical solutions of the present invention and not for limiting, and although the present invention is described in detail with reference to examples, it should be understood by those skilled in the art that modifications or equivalent substitutions may be made to the technical solutions of the present invention without departing from the spirit and scope of the technical solutions of the present invention, which should be covered by the claims of the present invention.

The invention claimed is:

1. A method for preparing an antibacterial medical biomaterial, comprising:
   a) placing an acellular small intestinal submucosal matrix material in a sodium hydroxide solution containing sulfadiazine, and controlling pH of the solution between 7.1 and 13.0, so as to obtain an intermediate material loaded with sulfadiazine sodium on the surface and/or inside thereof;
   b) after removing the intermediate material obtained in step a from the solution, washing the same with a sodium chloride solution, and then performing a drying treatment, soaking the intermediate material in a silver nitrate solution, and substituting sodium ions on a sulfadiazine sodium pyrimidine with silver ions in the silver nitrate to obtain an acellular small intestinal submucosal matrix material loaded with sulfadiazine silver;
   c) performing a surface plasma treatment on the acellular small intestinal submucosal matrix material loaded with sulfadiazine silver obtained in step b to hydroxylate a surface of the acellular small intestinal submucosal matrix material;
   d) coating a layer of antibacterial gel layer on the surface of the acellular small intestinal submucosal matrix material in step c, wherein the antibacterial gel layer and the acellular small intestinal submucosal matrix material are combined by hydrogen bonding;
   e) after absorbable fibers are subjected to plasma treatment, preparing the absorbable fiber solution or gel liquid, and then stirring the sulfadiazine silver and the absorbable fiber solution or gel liquid uniformly to obtain a mixed solution or a mixed gel liquid;
   f) coating the mixed solution or mixed gel liquid in step e on the surface of the acellular small intestinal submucosal matrix material with the antibacterial gel layer prepared in step d, and placing the acellular small intestinal submucosal matrix material in an oven or freeze-drying to obtain an antibacterial medical biomaterial.

2. The method for preparing an antibacterial medical biomaterial according to claim 1, wherein the step b further comprises: soaking the acellular small intestinal submucosal matrix material loaded with sulfadiazine silver in a compound buffer solution of PH 7.5~11.0; after the reaction is performed under the conditions of microwave irradiation, the surface of the acellular small intestinal submucosal matrix material loaded with sulfadiazine silver is formed with a compound film, washing and drying the acellular small intestinal submucosal matrix material loaded with sulfadiazine silver;

the compound buffer solution includes a buffer solution of one or more of chitosan, phenol sulfoethylamine, hemostatic polymer/compound, bioactive molecule, biomimetic active polypeptide molecule, polyamino acid, polydopamine, polyglycolide-trimethylene carbonate, polyglycolide and copolymers thereof, polycarbamone, poly L-lactide-caprolactone, polyglycolic acid, PPDO and PDO.

3. The method for preparing an antibacterial medical biomaterial according to claim 1, wherein the reactions in steps a and b are all performed in a thermostatic ultrasonic washer oscillating in a washing tank, and the ultrasonic shaking condition is that: 25~35° C. thermostatic reaction for 10~60 minutes, the oscillation frequency is 150~230 rpm, and the ultrasonic frequency is 40~50 kHz.

4. The method for preparing an antibacterial medical biomaterial according to claim 1, wherein the molar ratio of sulfadiazine to sodium hydroxide is 1:2~5, and the molar ratio of sulfadiazine to silver nitrate is 1:2~5.

5. The method for preparing an antibacterial medical biomaterial according to claim 1, wherein a method for preparing an acellular small intestinal submucosal matrix material comprises:
   a1) immersing a small intestinal submucosal tissue material on an animal body into physiological saline for washing, placing a clean small intestinal submucosal tissue material into a closed container, and performing lyophilization sealing and sterilization storing on the small intestinal submucosal tissue material in liquid nitrogen;
   b1) immersing the defrosted small intestinal submucosal tissue material into the decellularization solution for decellularization;
   c1) ultrasonically cleaning the small intestinal submucosal tissue material after decellularization treatment in a sodium chloride solution, and stopping cleaning the small intestinal submucosal tissue material when the conductivity of the small intestinal submucosal tissue material is 1.5 um/s or less to obtain the acellular small intestinal submucosal matrix material;

wherein when decellularization is performed by immersing the defrosted small intestinal submucosal tissue material into the decellularization solution, the decellularization is performed by treating the small intestinal submucosal tissue material obtained in step a1 with the decellularization solution in an environment containing two ultrasonic frequency wherein the decellularization solution comprises trypsin and PBS solution;

wherein the mass percentage concentration of trypsin in the decellularization solution is 0.05~0.3%, the concentration of PBS solution is 0.5~1.5 mmol/L, and the pH value of the decellularization solution is 7.0~8.0.

6. The method for preparing an antibacterial medical biological material according to claim 5, wherein the decellularization process is performed in a dual-frequency ultrasonic apparatus, wherein a low frequency range is 30~50 KHz, and a low frequency treatment for 10~45 min; a high frequency is 70~100 KHz, a high frequency treatment for 15~45 min, and a temperature range of the decellularization solution is 20~35° C.; ultrasonic power is 5000 W or more.

7. The method for preparing an antibacterial medical biomaterial according to claim 5, wherein a concentration of the sodium chloride solution is 0.01~0.05 mol/L, when the decellularized small intestinal submucosal tissue material is ultrasonically cleaned with sodium chloride solution.

* * * * *